US010434004B2

United States Patent
Nakamitsu

(10) Patent No.: US 10,434,004 B2
(45) Date of Patent: Oct. 8, 2019

(54) SHOULDER BRACE FOR NON-SURGICAL TREATMENT FOR ACROMIOCLAVICULAR JOINT DISLOCATION OR DISTAL CLAVICLE FRACTURE

(71) Applicant: Shin-ichi Nakamitsu, Fukuoka (JP)

(72) Inventor: Shin-ichi Nakamitsu, Fukuoka (JP)

(*) Notice: Subject to any disclaimer, the term of this patent is extended or adjusted under 35 U.S.C. 154(b) by 135 days.

(21) Appl. No.: 15/305,531

(22) PCT Filed: Apr. 30, 2014

(86) PCT No.: PCT/JP2014/062000
§ 371 (c)(1),
(2) Date: Oct. 20, 2016

(87) PCT Pub. No.: WO2015/166561
PCT Pub. Date: Nov. 5, 2015

(65) Prior Publication Data
US 2017/0035599 A1    Feb. 9, 2017

(51) Int. Cl.
*A61F 5/37*    (2006.01)

(52) U.S. Cl.
CPC .............. *A61F 5/3738* (2013.01); *A61F 5/37* (2013.01); *A61F 5/373* (2013.01)

(58) Field of Classification Search
CPC .......... A61F 5/3738; A61F 5/37; A61F 5/373; A61F 5/3723; A61F 5/3746;
(Continued)

(56) References Cited

U.S. PATENT DOCUMENTS 2,460,589 A * 2/1949 Lewis ................... A61F 5/3738
602/4
3,404,680 A * 10/1968 Guttman ............... A61F 5/3738
602/4
(Continued)

FOREIGN PATENT DOCUMENTS

JP    2003010219    1/2003
JP    2004261531    9/2004

OTHER PUBLICATIONS

Cover page A.L. Kapandji. Anatomie fonctionnelle 1: Membres superieurs. Physiologie de l'appareil locomoteur, sixth edition printed in color, Ishiyaku Publishers, Inc., May 2006.

*Primary Examiner* — Kari K Rodriquez
(74) *Attorney, Agent, or Firm* — Shlesinger, Arkwright & Garvey LLP

(57) ABSTRACT

A shoulder brace for non-surgical treatment that is capable of immobilizing an upper arm of a patient having acromioclavicular joint dislocation or a distal clavicle fracture. The brace enables activities of daily living for the patient and relieves uneasiness/discomfort. The shoulder brace includes a strap utilized for reduction, the strap forming a loop made in series by a section which runs down vertically from the front of the acromioclavicular joint toward the ulnar side of the forearm, a section which runs across a forearm trough, a section which runs up from the radial side of the forearm windingly across the front of the upper arm to the back of the shoulder, and a section which runs across from the back to the front over the shoulder pad and reaches to the acromioclavicular joint part. The shoulder brace is fitted to a patient in the extremity position where the upper arm hangs down, and the strap runs crossly or twistingly to stably retain the reduction.

5 Claims, 11 Drawing Sheets

(58) Field of Classification Search
CPC .... A61F 5/0118; A61F 5/013; A61F 5/05858; A45F 3/14; A45F 2003/146; A47D 13/025
USPC ...................................................... 602/4, 20
See application file for complete search history.

(56) References Cited

U.S. PATENT DOCUMENTS

| | | | | |
|---|---|---|---|---|
| 3,730,164 | A * | 5/1973 | Rash | A61F 5/3738 602/4 |
| 4,188,944 | A * | 2/1980 | Augustyniak | A61F 5/05808 602/20 |
| 6,099,489 | A * | 8/2000 | Herzberg | A61F 13/10 128/876 |
| 6,190,340 | B1 * | 2/2001 | Borell | A61F 5/3738 2/44 |
| 9,044,324 | B2 * | 6/2015 | Krenzel | A61F 5/3738 |
| 2002/0007133 | A1 * | 1/2002 | Givler | A61F 5/3738 602/20 |
| 2003/0135141 | A1 | 7/2003 | Berhorst | |

* cited by examiner

SHOULDER BRACE FOR NON-SURGICAL TREATMENT FOR ACROMIOCLAVICULAR JOINT DISLOCATION OR DISTAL CLAVICLE FRACTURE

TECHNICAL FIELD

The present invention relates to a brace for giving treatment without an operation for acromioclavicular joint dislocation or distal clavicle fracture and relates to a brace for treating a fracture which is prescribed by an orthopaedic surgeon or a sports medicine specialist and capable of performing reduction and retention. In addition, the present invention offers a shoulder brace for immobilizing an upper extremity of a patient who suffers acromioclavicular joint dislocation or distal clavicle fracture and relates to a shoulder brace for non-surgical treatment capable of reducing restrictions on the activities of daily living or rehabilitation of the patient to minimum requirements.

BACKGROUND ART

Acromioclavicular joint dislocation corresponds to luxation or subluxation of the distal clavicle end of a patient (refer to reference numeral 11 of FIG. 11A) which can be caused by rupture or injury of the acromioclavicular ligament and the coracoclavicular ligament suffered when the patient falls over and directly hits the shoulder in sports such as rugby, hockey and cycling. It is a disorder in which the clavicle is dislocated upward from the scapular acromion. On the other hand, distal clavicle fracture is a disorder in which a fracture is suffered in a part of the clavicle near the shoulder to dislocate a part of the bone upward.

Acromioclavicular joint dislocation or distal clavicle fracture is reduced by pressing down the clavicle dislocated upward and retaining it for a specific period of time. For the purpose of the reduction, several types of braces for non-surgical treatment are placed on the market.

RELATED ART DOCUMENTS

Patent Document

Patent Document 1: Japanese Patent Laid-Open Publication No. 2004-261531

Non-Patent Document

Non-Patent Document 1: A. L. Kapandji. *Anatomie fonctionnelle* 1: *Membres supérieurs. Physiologie de l'appareil locomoteur*, sixth edition printed in color, Ishiyaku Publishers, Inc., May 2006

SUMMARY OF THE INVENTION

Problems to be Solved by the Invention

Conventionally, as the brace for treating acromioclavicular joint dislocation or distal clavicle fracture, a sling or an arm support of the so-called gun-slinger type can be temporarily employed in the initial stage of non-surgical treatment for acromioclavicular joint dislocation or distal clavicle fracture. However, a sling or an arm support is utilized not for making a functional recovery from the disorder, but for reducing the pain. In a shoulder disorder, the scapula is drawn downward by the weight of the upper extremity to apply a shearing force to the disorder part, and hence, keeping the upper extremity below would increase the pain. Supporting the forearm with a sling or an arm support is slightly useful for reducing the pain. However, a sling or an arm support does not include a strap or the like arranged in the part of the acromioclavicular joint, and thus, the clavicle cannot be returned to its anatomically natural position and retained there.

In addition, another type of brace for treating acromioclavicular joint dislocation or distal clavicle fracture is conventionally employed which links the clavicle and the elbow using a strap in front of the body. The strap arranged over the shoulder has a shoulder pad attached thereto for pressing the clavicle. However, a patient has the shoulder inclined from the neck toward the acromion, and thereby, the shoulder pad can move to the outside of the acromioclavicular joint/the side of the acromion and then slip down easily. Particularly, if a patient moves the elbow outward or backward when putting on or taking off clothes or taking a decubital position, then the shoulder joint rotates, and thereby, the strap and the shoulder pad may frequently move toward the outside of the shoulder and slip down from the shoulder. Further, when a patient is walking with the above brace on and the strap linking the clavicle and the elbow in front of the body, the forearm swings laterally over and over again, thereby moving the strap and the shoulder pad toward the outside of the shoulder and slipping them from the shoulder.

Therefore, the Kenny-Howard Sling (registered trademark) shown in FIG. 11B is widely used. The Kenny-Howard Sling (registered trademark) includes, as shown in FIG. 11B, three straps in total: a first strap 12 which links the acromioclavicular part and the part of a forearm trough 14 adjacent to the elbow; a second strap 13 which links the part of the first strap 12 adjacent to the shoulder and the part adjacent to the armpit on the side opposite to the affected part in the lateral directions of the trunk, the second strap 13 being for preventing the first strap 12 from slipping down from the shoulder; and a third strap 15 which links the second strap 13 and the part of the forearm trough 14 adjacent to the wrist, the third strap 15 being for supporting the forearm stably.

However, as described above, the Kenny-Howard Sling (registered trademark) includes the three straps 12, 13 and 15 in total, and hence, it would be difficult for a patient to fit it alone while protecting the affected part. Besides, if a patient uses the Kenny-Howard Sling (registered trademark), then a strap crosses the breast, thereby making the patient feel uncomfortable with it on.

Furthermore, when the conventional Kenny-Howard Sling (registered trademark) is fitted to a patient for treating acromioclavicular joint dislocation or distal clavicle fracture, the wrist and the hand and fingers are set at the flank on the unaffected-part side opposite to the affected-part side. The forearm is held such that the longitudinal directions thereof are horizontal and lateral if seen from the patient, thereby imposing conspicuous restrictions on the activities of daily living using the hands and fingers of the upper extremities.

In treatment given to an athlete who has injured the acromioclavicular joint, a clinician or a physical therapist confronts some tasks, and one of the tasks is to protect the disorder part securely during the rehabilitation while keeping the athlete comfortable or mobile within a range of activities permitted by the clinician or physical therapist.

When a patient uses the conventional Kenny-Howard Sling (registered trademark), the forearm is held in the horizontal and lateral directions in front of the stomach. This can cause the patient to lose his/her posture balance when bending forward, or conversely, backward. Besides, the positions of the upper extremities are mutually different, and hence, an athlete may lose his/her lateral posture balance when training for the lower extremities or the trunk.

It is an object of the present invention to provide a shoulder-joint immobilizing brace capable of keeping the distal clavicle end at the same height level as the scapular acromion without interfering with movement of the body. In addition, it is an object of the present invention to provide a shoulder brace for non-surgical treatment which immobilizes an upper arm of a patient in an extremity position where the upper arm hangs down along the trunk in acromioclavicular joint dislocation or distal clavicle fracture, the shoulder brace for being capable of reducing the acromioclavicular joint dislocation or the distal clavicle fracture by pressing down and immobilizing (holding) the fractured part dislocated upward of the distal acromioclavicular joint or the distal clavicle end in the ulnar directions; preventing a strap on the shoulder from easily moving laterally and slipping down from the shoulder; fulfilling the functions of the wrist and the hand and fingers without hindrance to the activities of daily living; easily fitting the brace alone; and eliminating a hindrance to ordinary walking or rehabilitation for the lower extremities and thereby minimizing the inconvenience given through use of the shoulder brace for non-surgical treatment to the patient in his/her life, so that the patient can lead a smooth daily life.

Means for Solving the Problems

The present invention provides a brace which is capable of setting the upper extremity of a patient that undergoes treatment for acromioclavicular joint dislocation or distal clavicle fracture, not in front of the trunk as conventionally used but on the side of the trunk. This brace minimizes the daily-life inconvenience given to the patient undergoing treatment. In addition, the present invention provides a strap to be fitted to a patient, as described below, in a different shape from any conventional one, so that the strap can securely support the new extremity position.

Specifically, a shoulder brace for non-surgical treatment according to the present invention which includes a ringed strap to be fitted to a patient such that the distal clavicle end corresponding to a dislocated part in acromioclavicular joint dislocation or distal clavicle fracture is linked to a part of the forearm adjacent to the elbow, wherein: the ringed strap leads the upper arm of the patient hanging down along the side of the trunk, and leads the elbow flexed at an angle of approximately 80-100° and the forearm immobilized in an oblique and frontward direction from the trunk; and the ringed strap is fitted to the patient in a shape where the ringed strap (a) runs substantially vertically from the distal clavicle end toward a part of the ulnar side of the forearm adjacent to the elbow, (b) runs from the ulnar side of the forearm across the lower surface side of the forearm and turns to the radial side of the forearm, (c) runs from the radial side of the forearm across the front of the upper arm, and (d) runs up from the armpit on the affected-part side toward the back of the shoulder, and (e) runs through the back of the shoulder joint and reaches to the distal clavicle end.

In the above shoulder brace for non-surgical treatment, the forearm of the patient is immobilized at an angle of 20-40° of internally rotation of the shoulder on a horizontal plane of the shoulder.

Advantages of the Invention

The conventional immobilization of the arm and elbow of a patient in front of the body can cause tension in muscles of the shoulder or the upper arm. In contrast, the shoulder brace for non-surgical treatment for acromioclavicular joint dislocation or distal clavicle fracture according to the present invention immobilizes the shoulder and the upper extremity in the position different from the conventional one, and thereby, the upper extremity hangs down naturally to relieve tension in the shoulder intrinsic muscles and avoid fatigue in the muscles. Further, when the muscles of the upper extremity are relaxed, the upper extremity is settled in the hanging-down position, thereby making the upper extremity more stable. Still further, the upper extremity is kept in the hanging-down position on the side of the trunk, thereby preventing the posture of the patient from worsening.

When the shoulder brace for non-surgical treatment is fitted to a patient and the patient stays in a standing position, the brace is capable of changing the force of gravity acting on the upper extremity, through the link of the strap, into a force pressing down the clavicle, and thereby, reducing acromioclavicular joint dislocation or distal clavicle fracture. Besides, the brace according to the present invention is fitted with the strap twisted and thereby has a stronger friction force than any conventional uncrossed strap. This makes the upper extremity more stable.

In other words, according to the present invention, when a patient having the brace on stays in a standing position, the force of gravity acting on the forearm is changed into a force pressing down the distal clavicle end dislocated upward or the bone part fractured and dislocated upward. This makes it possible to reduce acromioclavicular joint dislocation or distal clavicle fracture.

In addition, even when the shoulder brace for non-surgical treatment is fitted and the patient stays in a decubital position where the force of gravity is not acting on the forearm, the strap linking the forearm and the elbow of the patient presses and holds the distal clavicle end or the fractured part dislocated upward of the patient in the ulnar directions of the forearm. This makes it possible to reduce and retain acromioclavicular joint dislocation or distal clavicle fracture. Furthermore, in the shoulder brace for non-surgical treatment according to the present invention, the front part and back part of the strap run parallel with the humerus, and the center of rotation of the humerus is located near the center of turn of the strap. This makes the strap more stable at the time when the patient makes a turning motion such as changing the posture from a sitting position to a supine position.

When a conventional brace is fitted to a patient, the hand and fingers/the forearm/the elbow are horizontally set in front of the body. Hence, when the patient is walking, the elbow tends to swing laterally, thereby frequently slipping the strap outward when walking. However, in the brace according to the present invention, the strap runs over the shoulder in directions approximate to the longitudinal directions of the forearm of the patient. Therefore, even when the patient is walking, the movement of the forearm can be prevented from drawing the strap laterally, thereby hindering a slip of the shoulder pad.

The strap according to the present invention is fitted to a patient, as described above, in a ring shape as a whole twisted at an angle of approximately 110-130° (preferably, approximately 120°). Hence, the directions in which the ringed strap runs under the lower surface of the forearm intersect at an angle of approximately 80-120° (preferably, approximately 90°) with the directions in which the ringed strap runs over the distal clavicle end. Specifically, the angle between the directions in which the strap runs over the distal clavicle end and the directions in which the strap runs under the lower surface of the forearm is 0°, as shown in FIG. 8A, when the longitudinal directions of the forearm extend parallel with the frontward directions from the trunk of the patient, while the angle is 90° in FIG. 8B. On the other hand, as shown in FIG. 8C, when the longitudinal directions of the forearm intersect at an angle of approximately 20-40° (preferably, approximately 30°) on the middle side of the trunk with the frontward direction from the trunk of the patient, as shown in FIG. 8C, the glenohumeral joint is internally rotated from the side of the trunk toward the middle of the trunk, for example, at an angle of approximately 30°. Accordingly, the directions in which the strap runs over the distal clavicle end intersect, for example, at an angle of approximately 80-120° (or approximately 90°) with the directions in which the strap runs under the lower surface of the forearm.

When the conventional Kenny-Howard Sling is fitted to a patient, the hand and fingers are set at the flank on the unaffected-part side. In contrast, when the brace according to the present invention is fitted to a patient, the wrist and the hand and fingers are set in front of the body of the patient. Therefore, the patient is able to work using the hand easily in front, and further, work using the hand together with the hand on the unaffected-part side, such as reading and notetaking.

When the Kenny-Howard Sling described above is fitted to a patient, the arm of the patient is suspended by the three straps: the first strap which runs vertically for performing reduction and retention; the second strap which runs crossly for drawing the shoulder pad inward; and the third strap for suspending the wrist. This complicates the strap system, thereby making it hard to fit the Kenny-Howard Sling alone until the patient grows accustomed to. In contrast, the shoulder brace according to the present invention dispenses with the lateral strap to simplify the strap system. Besides, the shoulder brace enables the patient to use the hand and fingers on the affected-part side, so that the patient can fit and adjust the shoulder brace easily by himself/herself.

When the conventional brace is fitted to a patient, the forearm is set in front of the stomach, and this position is asymmetrical in the right-and-left directions if seen from ahead of and behind the patient and is also asymmetrical in the front-and-back directions of the patient if seen from sideways. Accordingly, it would be difficult for the patient to maintain his/her posture balance during rehabilitation. In contrast, when the brace according to the present invention is fitted to an athlete, the upper extremity is in a state approximate to its naturally hanging position on the side of the body. If the athlete sets the upper extremities such that the upper-extremity position on the unaffected-part side becomes the same as the upper-extremity position on the affected-part side, then the athlete can maintain his/her balance more easily. This enables the athlete to exercise using an ergometer or by jogging.

In addition, according to the present invention, when the above twisted ringed strap is fitted to a patient, the rotation angles (from the outside of the trunk toward the middle of the trunk) of the longitudinal direction of the forearm and the shoulder joint of the patient are stably kept at angles of approximately 20-40° (preferably, approximately 30°) if the frontward direction from the trunk is defined as an angle of 0°. As a result, even when the brace according to the present invention is fitted and the patient stays in a standing position, is walking or doing another such, the conventional fact can be evaded that "the longitudinal directions of the forearm of the patient are held laterally if seen from the patient". In other words, the longitudinal directions of the forearm of the patient are extended and held in the front-and-back directions if seen from the patient, and the hand and fingers of the patient are also held in front of the trunk. Therefore, when the patient is ordinarily walking or doing rehabilitation exercise for the lower extremities, the forearm is prevented from swinging laterally if seen from the patient or hitting the abdomen of the trunk. In summary, the strap for reducing acromioclavicle joint dislocation or distal clavicle fracture is fitted to a patient, thereby eliminating a hindrance to ordinary walking or rehabilitation for the lower extremities and minimizing the inconvenience given through use of the brace to the patient in his/her life.

Figure 1:
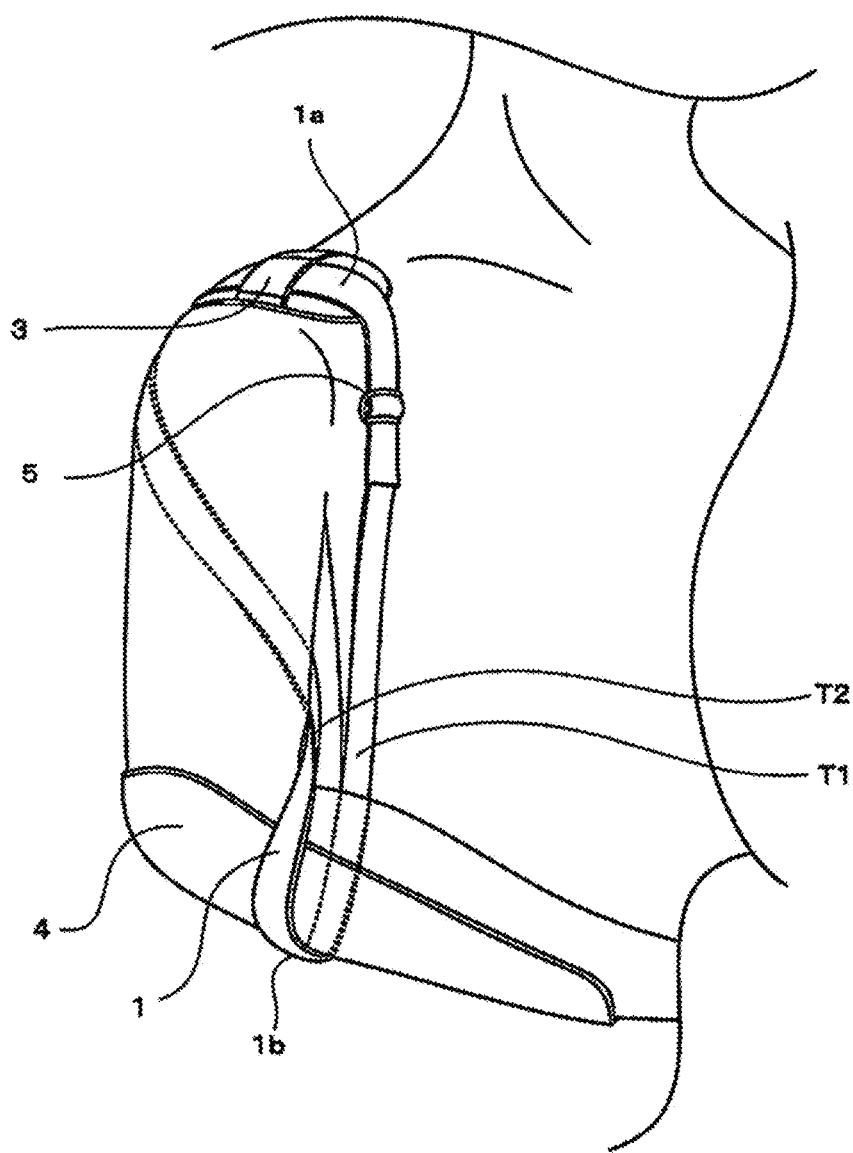
FIG. 1 is a perspective view of a ringed strap according to an embodiment of the present invention which is fitted between the shoulder and the upper arm of a patient.
Figure 2:
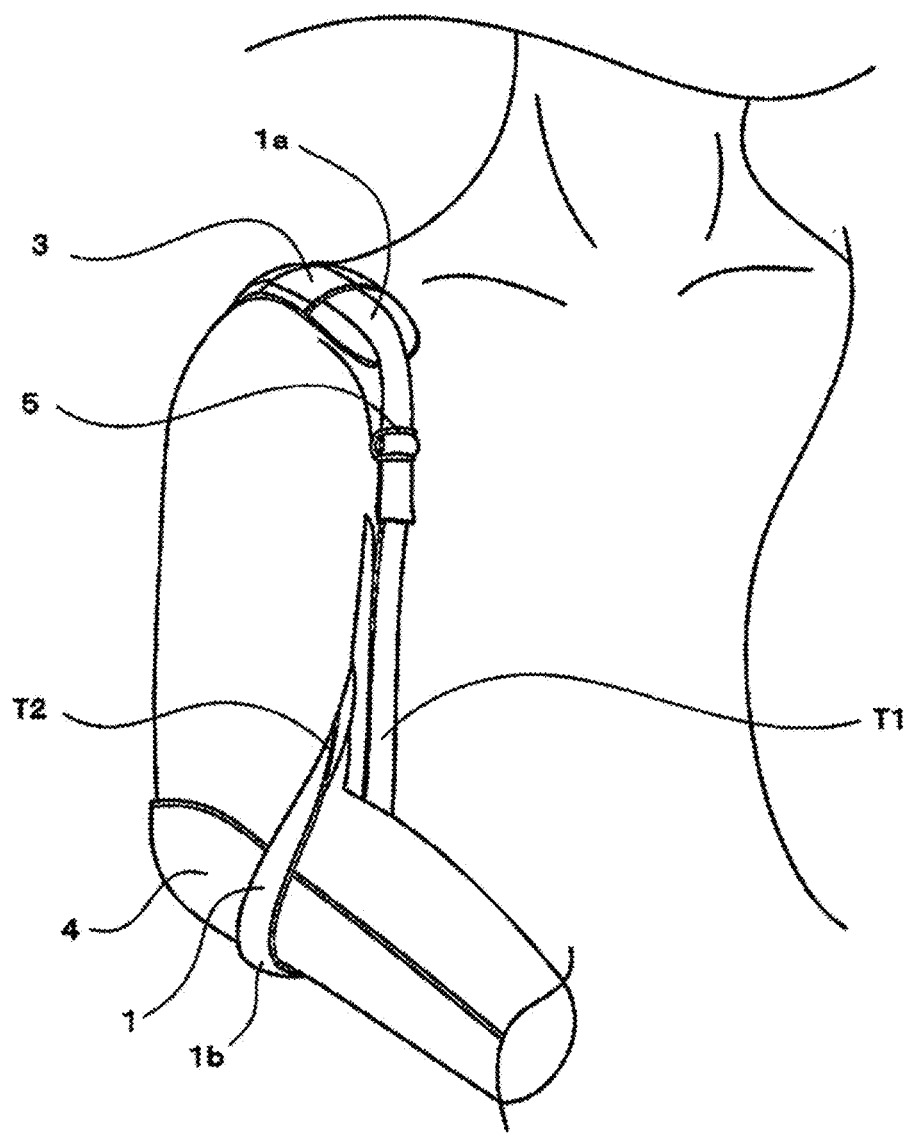
FIG. 2 is a perspective view of the ringed strap according to the embodiment of the present invention which is fitted between the shoulder and the upper arm of a patient.
Figure 3:
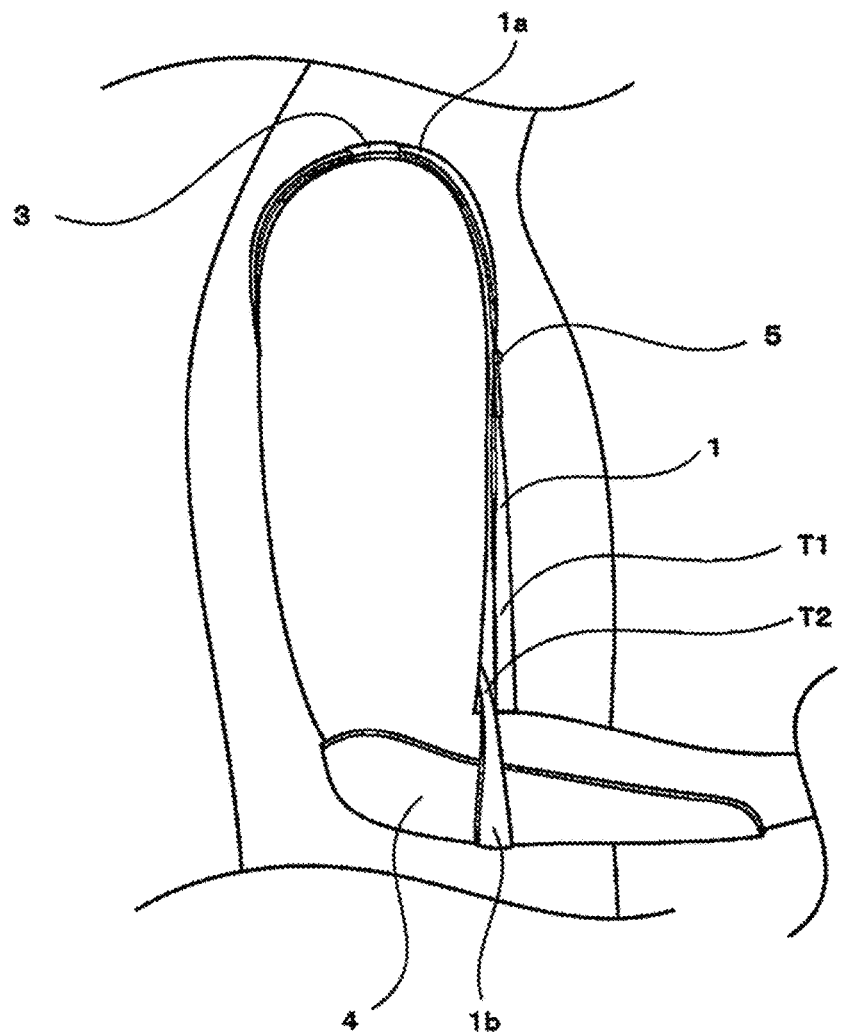
FIG. 3 is a perspective side view of the ringed strap according to the embodiment of the present invention which is fitted between the shoulder and the upper arm of a patient.
Figure 4:
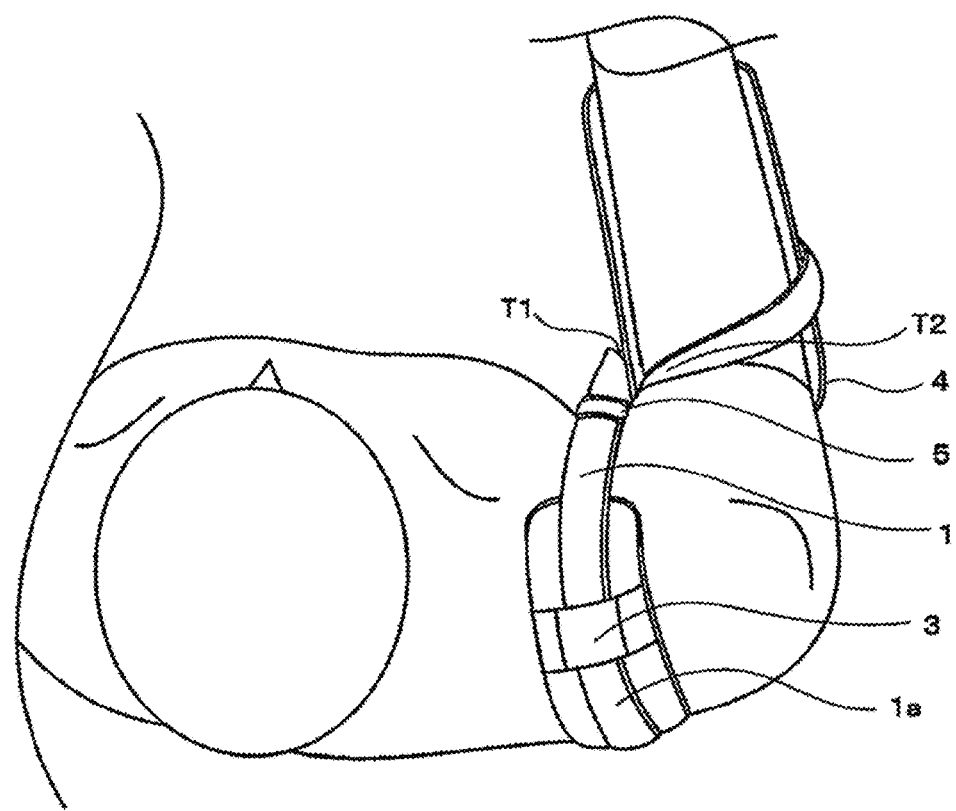
FIG. 4 is a perspective top view of the ringed strap according to the embodiment of the present invention which is fitted between the shoulder and the upper arm of a patient.
Figure 5:
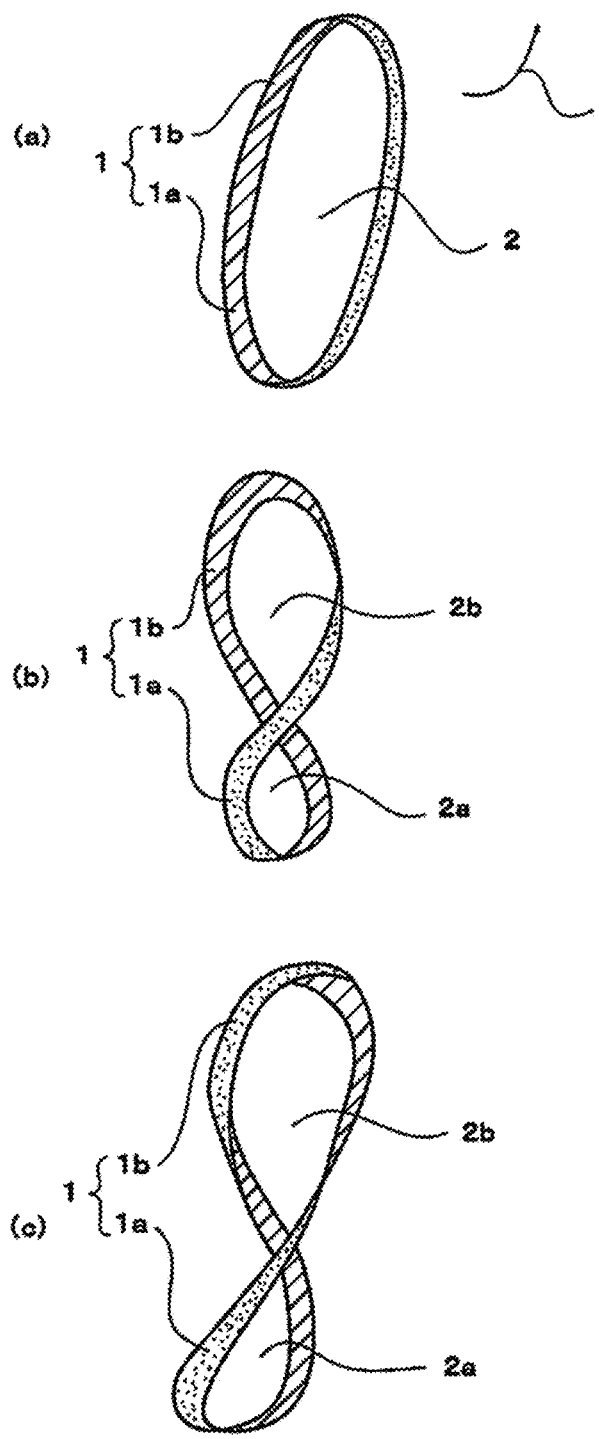
FIGS. 5A to 5C are illustrations showing how to form the ringed strap according to the embodiment into a twisted shape.
Figure 6:
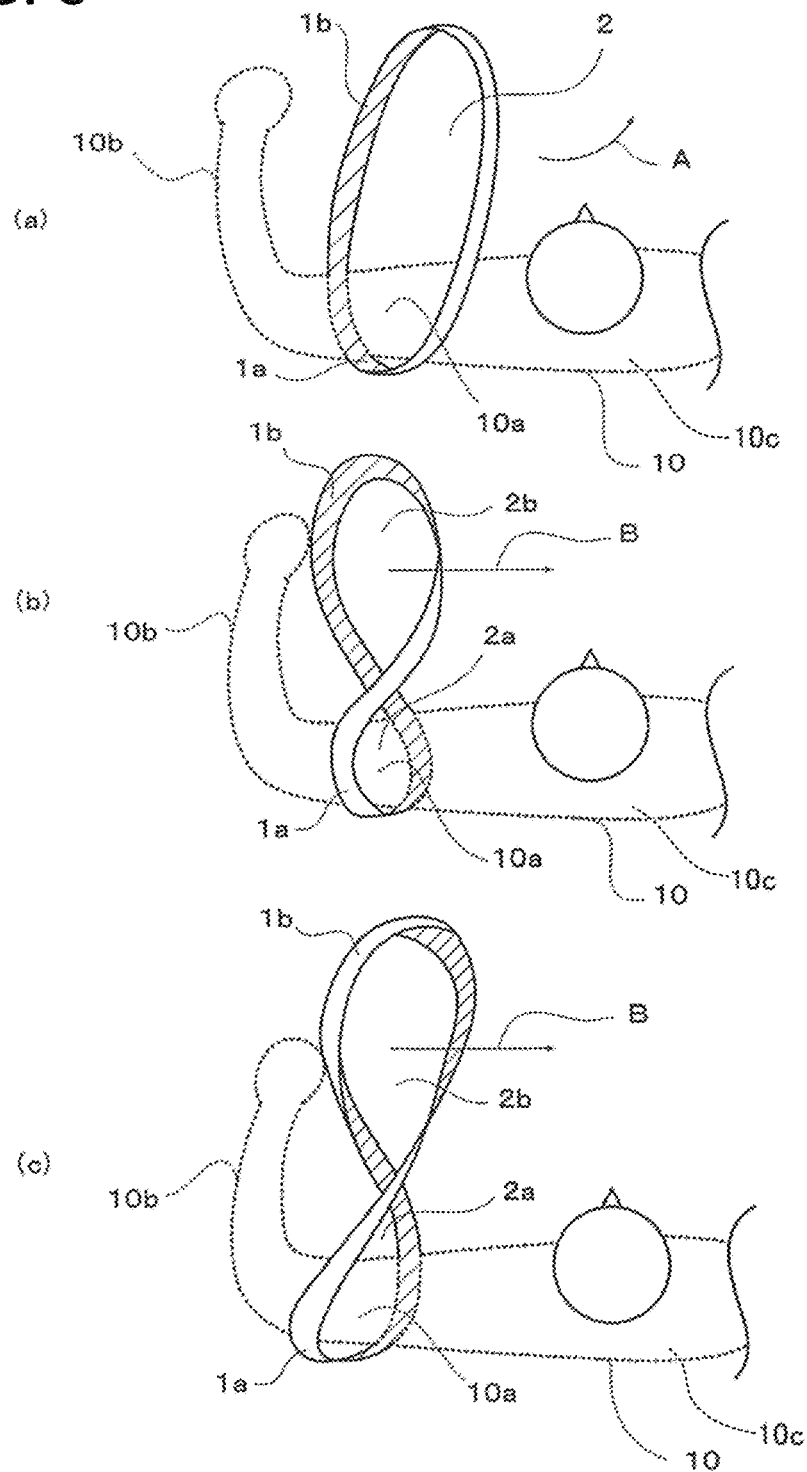
FIGS. 6A to 6C are illustrations showing how the ringed strap according to the embodiment is fitted to a patient.

FIGS. 1 to 4 are perspective views of a ringed strap in a shoulder brace for non-surgical treatment according to an embodiment of the present invention which is fitted between the shoulder and the upper arm of a patient. FIGS. 5A to 5C are illustrations showing how to form the ringed strap into a twisted shape. FIGS. 6A to 6C are illustrations showing how the ringed strap is fitted to a patient. FIGS. 7 and 8A-8C are illustrations showing advantages in the present invention. A detailed description of the following will be later given. When the shoulder brace for non-surgical treatment is fitted to a patient, the upper extremity hangs down along the trunk as a reference position thereof. In the reference position of the upper extremity, the longitudinal axis of the humerus agrees with a perpendicular line. The reference position of the upper extremity is an extremity position where the upper arm is not set in front of the trunk, in other words, where the upper arm is set on the side of the stomach. When the upper extremity is in the reference position, the upper arm is kept relaxed. (the shoulder flexion angle is 0° and the shoulder abduction angle is 0° which are defined by the Japanese Orthopaedic Association and the Japanese Association of Rehabilitation Medicine)

A detailed description of the following will be later given. When the shoulder brace for non-surgical treatment is fitted to a patient, the upper arm is hung down and the elbow is flexed at an angle of approximately 80-100° (preferably, approximately 90°) to direct the forearm frontward. If the rotation angle of the shoulder in this state is defined as 0°, then as the reference position about the rotation of the shoulder, the shoulder is internally rotated at an angle of approximately 30° on a horizontal plane. (the shoulder internal-rotation angle is 30° which is defined by the Japanese Orthopaedic Association and the Japanese Association of Rehabilitation Medicine)

In the shoulder brace for non-surgical treatment according to the present invention, as described above, "the shoulder is internally rotated at an angle of approximately 30° on a horizontal plane", and this rotation position corresponds to the reference position of the shoulder. The reason for this is that the shoulder is ahead of the lateral axis of the trunk and the glenohumeral joint is physiologically directed slightly inward from ahead of the trunk, in other words, that the group of rotator muscles is best-balanced. In this reference position of the shoulder regarding its rotation, the elbow joint of the patient is flexed at an angle of approximately 80-100° (preferably, approximately 90°), and the wrist and the hand and fingers of the patient are set in the oblique and frontward direction from the patient.

When the shoulder brace for non-surgical treatment which immobilizes the upper arm with hanging down along the side of the trunk is fitted to a patient, the ringed strap 1 linking the clavicle and a part of the forearm adjacent to the elbow is capable of reducing the upper arm and retaining the position. The ringed strap 1 is fitted in the shape described later which differs from the shape in which any strap employed for a conventional brace is fitted.

FIGS. 1 to 4 are used for reference. When the ringed strap 1 of the shoulder brace for non-surgical treatment is fitted to a patient, the ringed strap 1 forms a closed circuit. The ringed strap 1 of the shoulder brace for non-surgical treatment is fitted in the shape where the ringed strap (a) runs substantially vertically from the distal clavicle end toward a part of the ulnar side of the forearm adjacent to the elbow, (b) runs from the ulnar side of the forearm across the lower surface side of the forearm and turns to the radial side of the forearm (the side away from the trunk), (c) runs from the radial side of the forearm across the front (if seen from the trunk) of the upper arm, (d) runs up from the armpit on the affected-part side toward the back of the shoulder, and (e) runs across the back of the shoulder joint and reaches to the distal clavicle end. The distal clavicle end is a part dislocated upward in acromioclavicle dislocation or distal clavicle fracture, which is used for indicating the position to which the upper-end part of the ringed strap 1 is set. The ulnar side of the forearm corresponds to the inside of the forearm and the radial side of the forearm corresponds to the outside of the forearm.

When a conventional brace is fitted to a patient, the vertical part of a strap for reduction is not twisted with respect to the longitudinal axis of the upper arm. In contrast, when the ringed strap 1 of the shoulder brace for non-surgical treatment according to the present invention is fitted to a patient, the vertical part of the ringed strap 1 is twisted with respect to the longitudinal axis of the upper arm. Specifically, the ringed strap 1 is twisted (bent) by an angle of approximately 90° in a first direction (right or left direction) from its orientation on the front of the clavicle and reaches to the ulnar side of the forearm. Then, the ringed strap 1 is twisted by an angle of approximately 180° in a second direction opposite to the first direction while running from the radial side of the forearm up to the back of the shoulder (for example, from its orientation on the radial side of the forearm, the ringed strap: is twisted by an angle of approximately 90° in the second direction opposite to the first direction; in the orientation, runs across the front of the upper arm; near the armpit, is further twisted by an angle of approximately 90° in the second direction; and runs toward the distal clavicle end).

In the shoulder brace for non-surgical treatment according to the present invention, the ringed strap 1 forms the closed circuit, and a part of the ringed strap 1 comes close to another part thereof at a middle part of the upper arm without any mutual contact. Hence, the ringed strap 1 forms two rings. The shoulder and the forearm are retained with individually inserted into the two rings. The two rings are twisted each other at the approaching part of the ringed strap 1, for example, at an angle of approximately 110-130°. In other words, if seen from above, the directions in which the ringed strap 1 runs over the shoulder or a shoulder pad 3 intersect at an angle of approximately 80-120° (e.g., approximately 90°) with the directions in which the ringed strap 1 runs under the lower surface of the forearm or the lower surface of a forearm trough 4 (refer to an angle α of FIG. 8C described later).

The shoulder brace for non-surgical treatment is fitted to a patient during an acute period in the following method. A surgeon or an assistant flexes the elbow of the patient by an angle of approximately 90°, raises the elbow from below and presses down the clavicle subjected to protrusion from above to perform a manipulative reduction. Next, the surgeon or the assistant winds the ringed strap 1 (including the shoulder pad 3 or the forearm trough 4) around the shoulder and the upper extremity and closes the circuit of the ringed strap 1 by means of a hook. Then, the surgeon or the assistant checks on the degree of reduction by direct vision, or an x-ray to adjust the tightness of the ringed strap. In another method for fitting the shoulder brace to the patient, first into the ring of the ringed strap formed with a closed circuit, the upper arm and the shoulder are inserted, then the ring is simply twisted to form the other ring, and the forearm is inserted into the lower ring. This enables the patient to substantially fit the shoulder brace. The latter method facilitates fitting and removing the brace, so that an athlete can fit the brace by himself/herself if he/she grows accustomed to.

As described above, the shoulder brace for non-surgical treatment according to the present invention offers the shoulder brace which immobilizes an upper arm of a patient in a an extremity position where the upper arm hangs down along the side of the trunk in acromioclavicular joint dislocation or distal clavicle fracture, includes the ringed strap 1 forming the loop made in series by: the section which runs down vertically from the distal clavicle end toward the ulnar side of the forearm; the section which runs across the lower surface of the forearm (the lower surface of the forearm trough 4); the section which runs up from the radial side of the forearm across the front of the upper arm to the back of the shoulder; and the section which runs across from the back to the front over the shoulder pad 3 and reaches to the distal clavicle end.

Furthermore, in the shoulder brace for non-surgical treatment according to the present invention, the ringed strap 1 may be provided with a the shoulder pad 3 for preventing a skin decubitus ulcer in the position where the ringed strap comes into contact with or is arranged at the shoulder of a patient. Instead of the shoulder pad 3, an adhesive sheet applied to the skin may also be utilized.

Moreover, in the shoulder brace for non-surgical treatment according to the present invention, the ringed strap 1 is provided with a forearm trough (pouch) 4 in the position where the ringed strap 1 comes into contact with or arranged at the forearm of a patient.

In addition, the shoulder brace for non-surgical treatment according to the present invention includes a length adjusting portion 5 for changing the length of the ringed strap 1 which is arranged in the circuit of the ringed strap 1. The length of the ringed strap 1 is adjusted, enabling the ringed strap 1 to tightly link the shoulder and the elbow and to stabilize the shoulder joint.

In FIGS. 1 to 6, reference numeral 1 denotes a ringed strap which is made of, for example, cloth or resin and formed by a belt-shaped member having a width of approximately 0.5-5 cm (more preferably, approximately 1-3 cm); 3 denotes a shoulder pad (having the same formation as a conventional brace) attached to the top part in the figure of the ringed strap 1; 4 denotes a well-known forearm trough (a pad or a pouch coming into contact with a part of the forearm adjacent to the elbow) attached to the bottom part in the figure of the ringed strap 1; 5 denotes a length adjusting portion having a well-known formation for adjusting the whole length of the ringed strap 1 individually in accordance with the distance between the distal clavicle end and the forearm of each patient; T1 denotes a part of the ringed strap 1 which runs from the distal clavicle end to the ulna side of the forearm and twists at an angle of, for example, approximately 90° toward the middle of the trunk with respect to the longitudinal axis of the upper arm; and T2 denotes a part of the ringed strap 1 which runs from the radial side of the forearm across the upper arm to the back of the shoulder and twists as a whole at an angle of, for example, approximately 180° with respect to the longitudinal axis of the upper arm. The twisted parts T1 and T2 may be turned rightward around the middle of the trunk of the patient (right turn) or may be turned leftward around the middle of the trunk of the patient (left turn), in other words, either turn is feasible.

In the shoulder brace for non-surgical treatment, the length of the ringed strap 1 is preset so as to be somewhat loosened (see FIG. 5A). A surgeon leads a patient hanging down the upper arm along the side of the trunk, lets the patient flex the elbow and supports the elbow in the state to realize the reference position of the upper arm and the reference position about the rotation of the shoulder. Next, the forearm and the upper arm of the patient are inserted into an opening portion 2 (see FIG. 5A) formed by the ringed strap 1, and the lower surface of the upper-end part (the shoulder pad 3 arranged at the upper-end part) of the ringed strap 1 is set on the distal clavicle end of the patient (see FIG. 6A). Subsequently, the surgeon leads the patient to insert the upper arm and the forearm into the ring formed by the ringed strap 1 and holds a the shoulder pad 3 and the forearm trough 4 in place. The surgeon presses the clavicle from above or pushes up the elbow from below, thereby performing a manipulative reduction. Further, the above distance of the ringed strap 1 is shortened to ensure the reduction and retention. Still further, the ringed strap 1 is tightened up to perform an additional reduction.

Next, in the ringed strap 1, a lower portion 1b located on the side of the trunk of the patient is twisted with respect to an upper portion 1a. If the lower portion 1b is not twisted, then the angle in the state is defined as 0°. For example, the lower portion 1b is twisted by an angle of approximately 110-130° (preferably, for example, approximately 120°), and thereby, the ringed strap 1 is shaped into two small upper and lower opening portions 2a and 2b (see FIG. 5B). A shoulder joint 10a of the patient is set inside of the upper opening portion 2a. FIG. 5A is a perspective view of the ringed strap 1 which is not twisted. FIG. 5B is a perspective view of the ringed strap 1 which is twisted in the arrow-A direction of FIG. 5A. FIG. 5C is a perspective view of the ringed strap 1 which is further twisted in the arrow-A direction of FIG. 5A

Subsequently, into the lower opening portion 2b, a forearm 10b of a patient 10 is inserted from the outside of a trunk 10c of the patient 10 toward the middle thereof (refer to the arrow B of FIGS. 6B and 6C).

If the ringed strap 1 is fitted to the patient 10 through the procedure, then the ringed strap 1 would generate a force which restores itself from the state where the ringed strap 1 is twisted to the initial state where it is not twisted (a force which turns the lower portion 1b of the ringed strap 1 around the forearm 10b of the patient 10 as the center of rotation from the middle of the trunk 10c toward the outside thereof). This force could operate so that the forearm 10b rotates around the shoulder joint 10a of the patient 10 as the center of rotation from the middle of the trunk 10c toward the outside thereof. The force applied by the ringed strap 1 is balanced with the force which naturally moves the longitudinal directions of the forearm 10b from ahead of the outside of the trunk 10c toward the middle thereof. Accordingly, if the angle in the state where the lower portion 1b of the ringed strap 1 is not twisted with respect to the upper portion 1a is defined as 0°, the ringed strap 1 may be twisted at an angle of approximately 110-130° (preferably, approximately 120°) from the outside of the trunk 10c of the patient 10 toward the middle of the trunk 10c, so that the extremity position of the patient 10 could be kept naturally stable.

Figure 7:
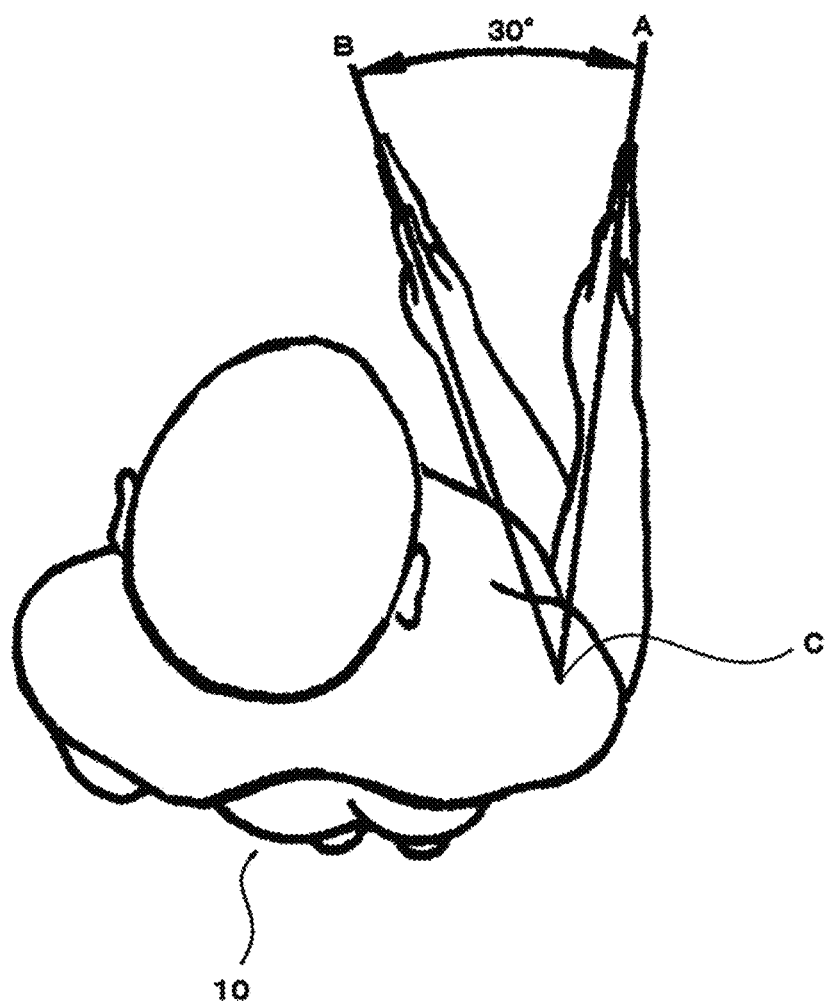
FIG. 7 is an illustration showing advantages in the embodiment.
Figure 8:
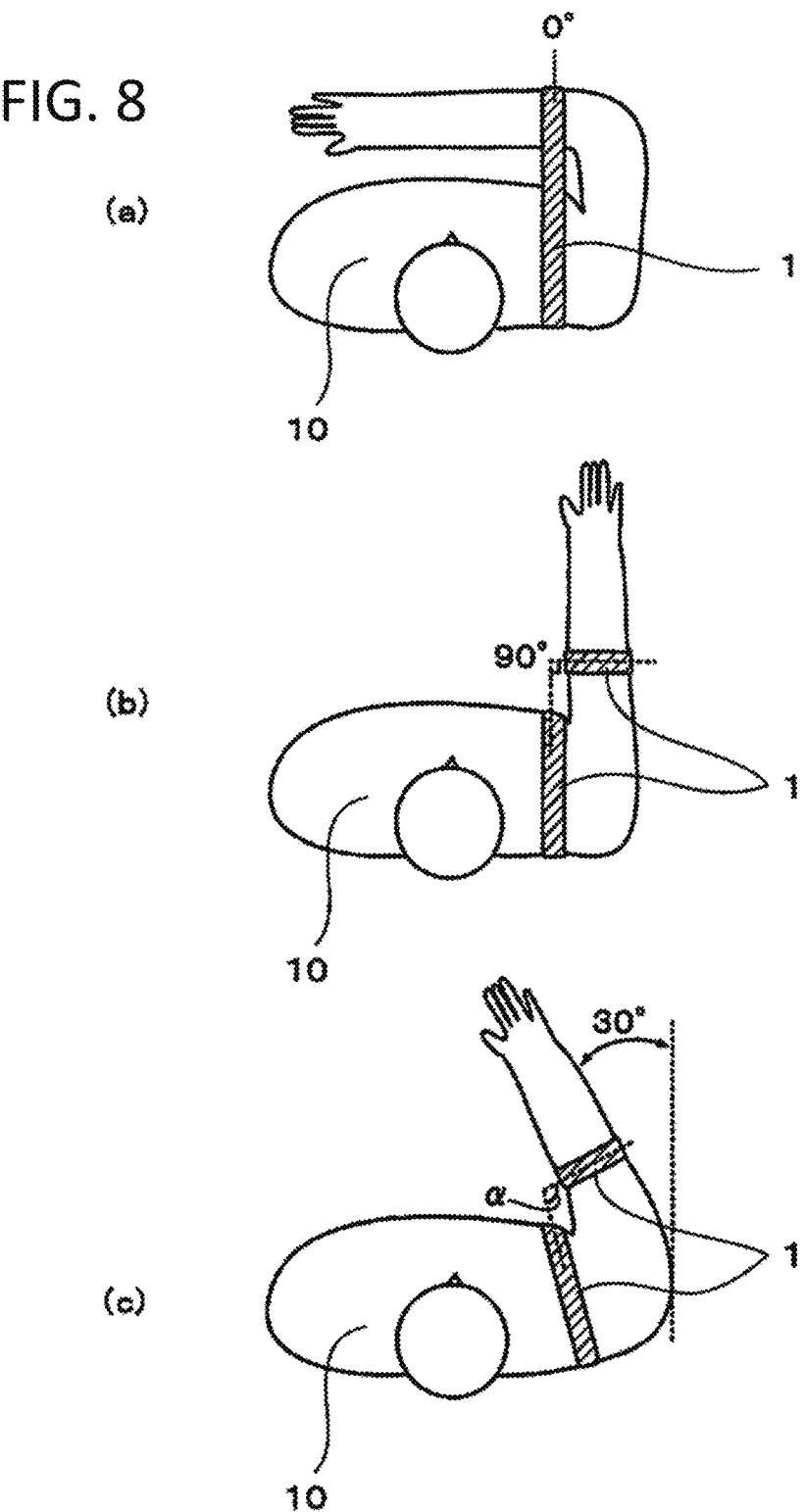
FIGS. 8A to 8C are illustrations showing advantages in the embodiment.
Figure 9:
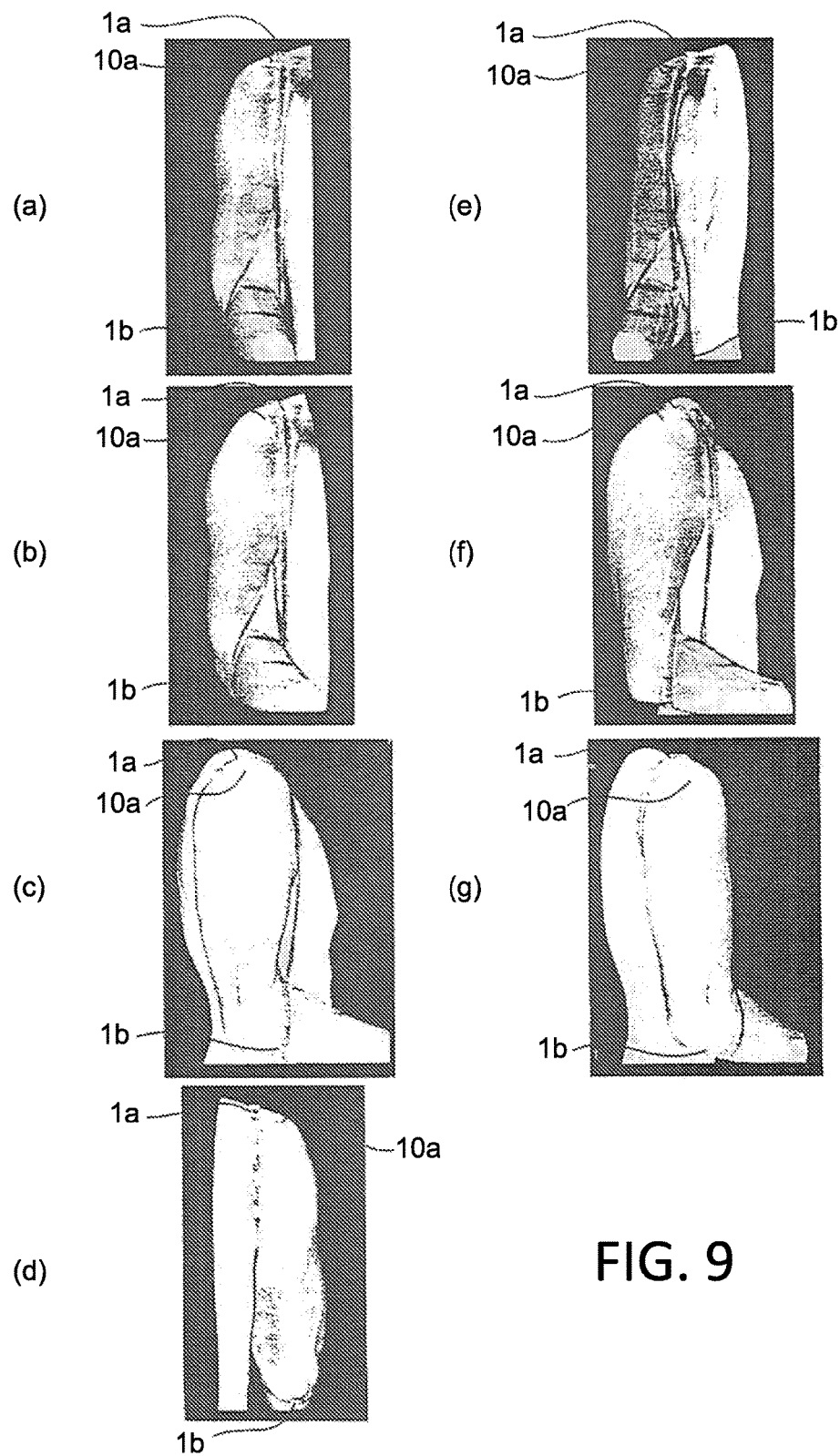
FIGS. 9A to 9G are photographs of the ringed strap according to the embodiment wrapped with stainless-steel foil which is fitted to a human body, the photographs being stereoscopic images each taken from a mutually different angle under soft-part conditions by the CT (Computed Tomography).
Figure 10:
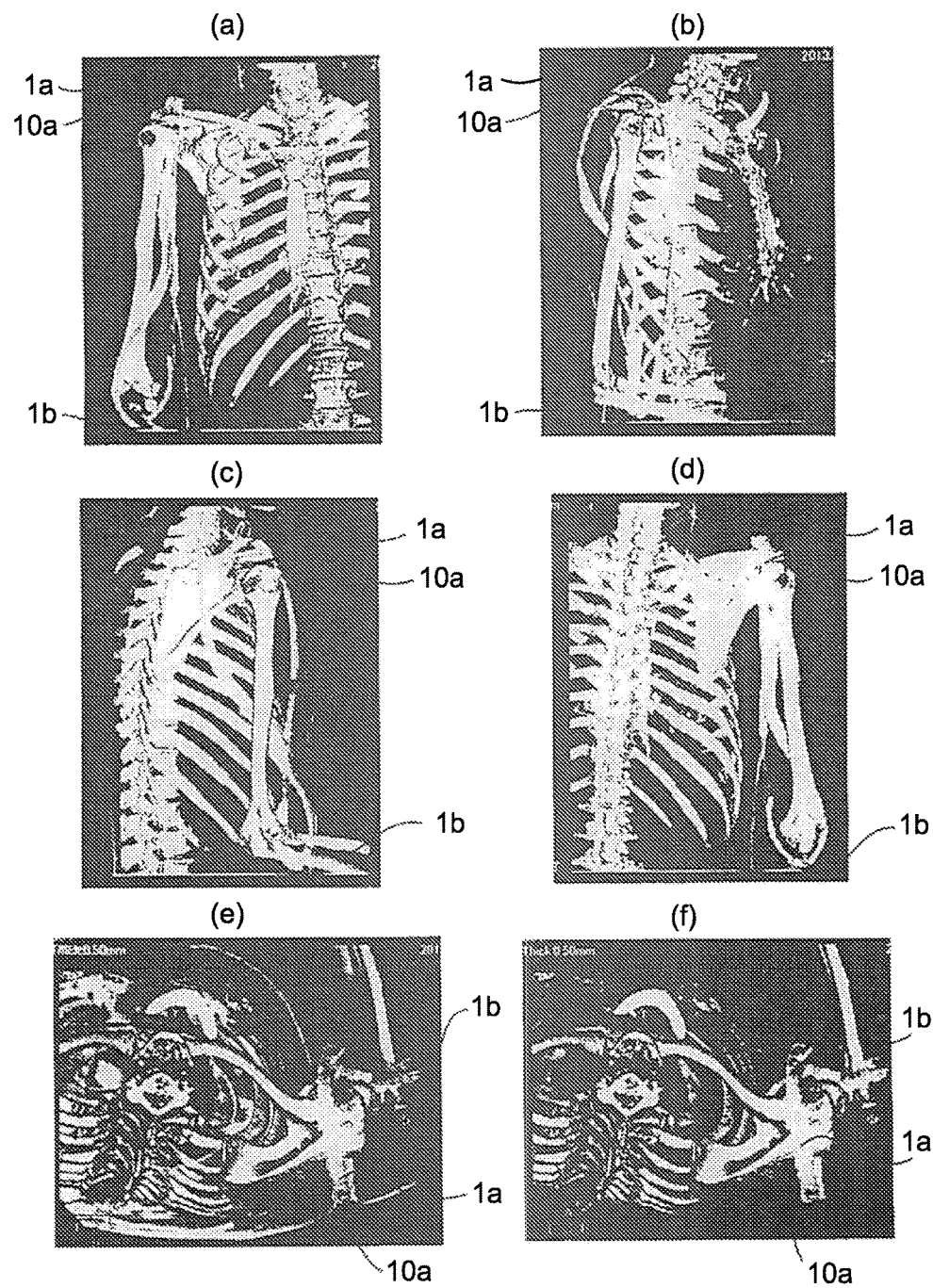
FIGS. 10A to 10F are photographs of the ringed strap according to the embodiment wrapped with stainless-steel foil which is fitted to a human body, the photographs being stereoscopic images each taken from a mutually different angle under bone conditions by the CT (Computed Tomography).
Figure 11:
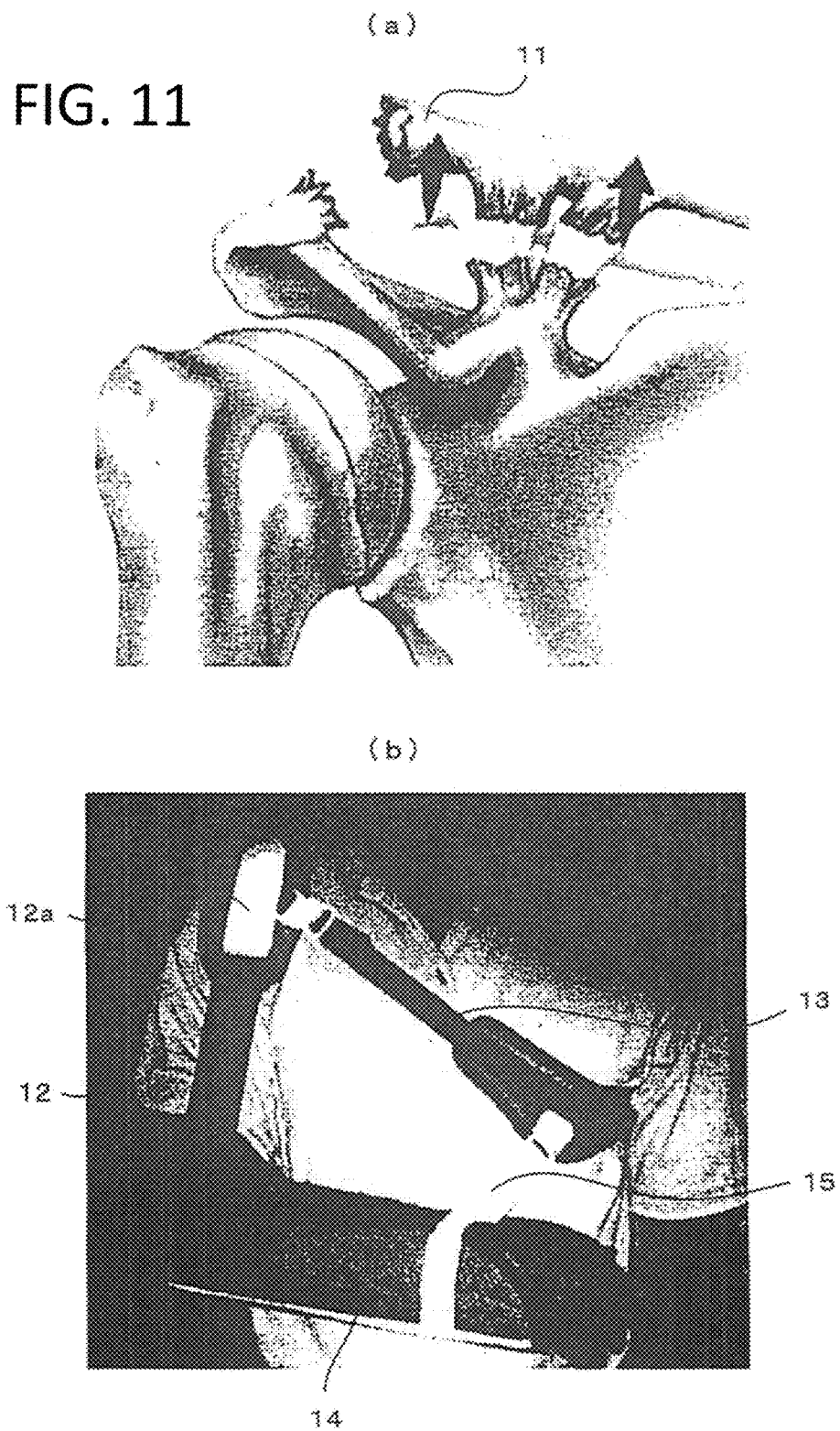
FIGS. 11A and 11B are an illustration and a photograph respectively showing a conventional brace for giving non-surgical treatment for clavicular joint dislocation.

The ringed strap 1 is twisted at an angle of, for example, approximately 110-130° (preferably, approximately 120°). Therefore, the longitudinal directions of the forearm 10b of the patient 10 and the shoulder joint 10a of the patient 10 are kept rotated (from the side of the trunk 10c toward the middle of the trunk 10c) at an angle of approximately 20-40° (preferably, approximately 30°) from the side of the trunk 10c of the patient 10 toward the middle of the trunk 10c (see FIG. 7), if the frontward direction (the upward direction in FIG. 7) from the trunk 10c of the patient 10 is defined as 0°, so that the extremity position of the patient 10 can be kept naturally stable. Specifically, in this case, as shown in FIG. 7, when the shoulder joint 10a of the patient 10 is rotated on a center C indicated in the figure, the forearm 10b is moved and the shoulder joint 10a is internally rotated by an angle of approximately 20-40° (preferably, approximately 30°) with respect to a direction A indicated in FIG. 7 (refer to a direction B indicated in FIG. 7). In other words, the longitudinal direction of the forearm 10b of the patient 10 agrees with the direction B of FIG. 7. This extremity position is the above "reference position of the upper arm" and "reference position about the rotation of the shoulder" (if necessary, below called a "neutral position"). The neutral position is a position where the shoulder joint 10a is kept unforced and natural.

Next, advantages in the embodiment of the present invention will be described with reference to FIG. 7, FIGS. 8A-8C and like. FIGS. 9A to 9G are photographs of the ringed strap of the shoulder brace for non-surgical treatment according to the present invention wrapped with stainless-steel foil which is fitted to a human body, the photographs being stereoscopic images each taken from a mutually different angle under soft-part conditions by the CT (Computed Tomography). FIGS. 10A to 10F are photographs of the ringed strap according to the embodiment wrapped with stainless-steel foil which is fitted to a human body, the photographs being stereoscopic images each taken from a mutually different angle under bone conditions by the CT (Computed Tomography). In FIGS. 9A-9G and FIGS. 10A-10F, reference numeral and character 10a denotes a shoulder joint.

It is desirable that a patient having the brace on could comfortably promote the activities of daily living. In order to promote the motion, the shoulder brace for non-surgical treatment according to the present invention is fitted to a patient and the forearm is set to the side of the trunk, as compared to an extremity position where the forearm of a patient having a conventional brace on is set in front of the stomach. One of the reasons why the shoulder brace is superior in extremity position is that the hand and fingers function better. In an extremity position where a conventional brace is fitted to a patient, the hand and fingers are set to the flank on the unaffected-part side, thereby imposing restrictions on utilization of the hand and fingers. In contrast, when the shoulder brace for non-surgical treatment according to the present invention is fitted to a patient, the hand and fingers are directed ahead of the trunk, enabling reading and note-taking.

Another reason is that when the patient changes the posture from a standing position or a sitting position to a supine position for sleeping, the patient can immobilize and hold the elbow more easily. If the patient having a conventional brace on stays in a supine position for sleeping, another strap for immobilizing the wrist or a pillow under the elbow is necessary for preventing the forearm from slipping to the side of the body. Besides, in an extremity position where a conventional brace is fitted to a patient, the forearm is set in front of the stomach, and the elbow is set frontward from the shoulder. Accordingly, when the patient is walking, the forearm swings laterally and hence the shoulder joint considerably moves right and left (laterally), thereby causing the shoulder pad to slip laterally.

In contrast, if the shoulder brace for non-surgical treatment according to the present invention is fitted to a patient and the upper extremity is immobilized in the neutral position, then when the patient is walking, the forearm moves back and forth, and hence, the shoulder joint moves back and forth as well. In other words, the shoulder joint will hardly move right and left, so that the shoulder can be held in the same position. Therefore, when the shoulder brace for non-surgical treatment according to the present invention is fitted to a patient, the forearm and the shoulder joint swing back and forth while walking. However, the elbow is located right below the shoulder, and hence, the forearm and the shoulder joint swing back and forth within a narrow range, and the strap on the distal clavicle end only moves back and forth and hardly moves right and left. This prevents the strap or the shoulder pad from easily slipping down from the shoulder.

Furthermore, when the shoulder brace for non-surgical treatment according to the present invention is fitted to a patient, in order to hold the elbow at an angle of approximately 90° when fatigue is accumulated in the muscles of the upper arm and the forearm 10b, another strap may be provided which is capable of holding the hand joint in a position necessary for holding (immobilizing) the elbow joint at an angle of approximately 90°. In this case alike, the patient moves the hand and fingers freely without restrictions.

When a conventional brace is fitted to a patient, the forearm is set in front of the stomach, and the wrist and the hand and fingers are held (immobilized) at the flank on the side opposite to the affected-part side with respect to the trunk. This position imposes conspicuous restrictions on the activities of daily living of the patient. In contrast, when the shoulder brace for non-surgical treatment according to the present invention is fitted to a patient, the hand joint and the hand and fingers are set in front of the side of the trunk, enabling reading, note-taking and the like, in short, easing restrictions on the operation of the upper extremity. Further, the patient can grip the handlebars or the like of an ergometer with both hands, so that the patient can work earlier at muscular-strength training in the lower extremities. Still further, even when the patient takes a rest by changing the posture from a sitting position to a supine position, the elbow is in close contact with the side of the trunk, and thereby, the immobilization of the shoulder and the elbow by the brace can be kept more easily than a conventional brace. Still further, even while the patient is asleep in the night, the shoulder brace dispenses with setting the forearm right over the stomach which is required for a conventional brace, and it also dispenses with a pillow under the forearm or the elbow which is required in a conventional brace. Therefore, the patient having the shoulder brace on can spend a sleeping time more comfortably In addition, when a conventional brace is fitted to a patient, the directions in which the strap runs over the shoulder joint are parallel to the directions in which the strap runs across the lower surface of the forearm, and the forearm is set in front of the stomach. Accordingly, while the patient is walking or when the patient moves the upper arm toward the side of the trunk, the strap on the shoulder joint may slip down easily from the shoulder. In contrast, when the shoulder brace for non-surgical treatment according to the present invention is fitted to a patient, the directions in which the ringed strap 1 runs over the distal clavicle end intersect at an angle of approximately 80-120° (preferably, approximately 90°) with the directions in which the ringed strap 1 runs across the lower surface of the forearm (refer to the angle α of FIG. 8C). Consequently, the shoulder and the forearm are tightly linked together, thereby narrowing the movement range of the elbow and the rotation angle of the shoulder joint while walking. As a result, when the patient is walking, the forearm and the shoulder joint hardly move in the right-and-left directions, but both move in the front-and-back directions, thereby almost preventing the ringed strap 1 from slipping down from the shoulder.

Furthermore, when the shoulder brace for non-surgical treatment according to the present invention is fitted to a patient, the shoulder joint is held (immobilized) in the neutral position, and hence, the upper arm hangs down vertically along the side of the trunk. Therefore, if observed from above the trunk, even when the shoulder joint is internally or externally rotated, the position of the center of rotation (refer to the reference character C of FIG. 7) of the humeral head remains unchanged. If the shoulder joint is internally and externally rotated, then the perpendicular line from the front of the shoulder to the ulnar side of the forearm adjacent to the elbow hardly moves because the perpendicular line is near from the humerus.

In the shoulder brace for non-surgical treatment according to the present invention, from the front, the side and the top, the ringed strap 1 looks as if one part and another part thereof were in contact with each other near the upper arm, but as a matter of fact, those parts are not in contact (see FIGS. 9A-9G and FIGS. 10A-10F). If seen from the front, one such part of the ringed strap 1 running through the front of the shoulder is set on the inside (the middle side of the trunk) from another such part of the ringed strap 1 running through the back of the shoulder (see FIGS. 9A-9G and FIGS. 10A-10F).

In the shoulder brace for non-surgical treatment according to the present invention, the ringed strap 1 is used with twisted at an angle of, for example, approximately 110-130° (preferably, approximately 120°). Accordingly, it is desirable that the ringed strap 1 should be made of a material which has the property of not stretching in the long-axis directions and generating a restoring force somewhat against a twist given thereto in the short-axis directions. However, the ringed strap 1 may be made of soft cloth or the like.

Next, the shoulder pad 3 provided in the ringed strap 1 will be described. If the ringed strap 1 of the embodiment is fitted directly to a patient, then the ringed strap 1 applies a pressure from above and a sideways friction force to the shoulder of the patient, which may produce a decubitus ulcer. Hence, it is desirable that the ringed strap 1 should be provided with the shoulder pad 3. Alternatively, the shoulder pad 3 can also be replaced with a sheet for the skin which is applied to the skin of the shoulder of the patient. As a gelled adhesive sheet for the skin, a sheet already placed on the market can be employed, such as a wound protective seal for medical care. If the patient uses such a sheet, then the sheet including an adhesive ingredient on its surface touching the skin adheres to the skin while the opposite outer surface has moderate friction which will not hinder the strap from sliding. This sheet is arranged as a buffer between the ringed strap 1 and the skin, thereby preventing the ringed strap 1 from producing a decubitus ulcer on the skin. Further, a surgeon or a physical therapist may put a mark on the sheet, and thereby, the patient can easily check whether the ringed strap 1 is positioned so as to press the clavicle. Still further, a thick block may be provided on the outside of the shoulder, which prevents the ringed strap 1 from slipping to the acromion.

The ringed strap is precisely set so as to press the distal clavicle end, thereby promoting reduction and retention of the affected part. However, if the ringed strap 1 slides outward on the shoulder and moves to the position in which it presses the acromion, that will bring about an adverse effect. Accordingly, it is important to check whether the ringed strap 1 is pressing the distal clavicle end, or whether it is not pressing the acromion by mistake. Further, for the purpose of the reduction, it is important to tighten the ringed strap 1 and keep the tension thereof.

REFERENCE NUMERALS 1 ringed strap
1a upper portion of a ringed strap
1b lower portion of a ringed strap
2 opening portion
2a upper opening portion
2b lower opening portion
3 shoulder pad
4 forearm trough
5 length adjusting portion
10 patient
10a shoulder joint
10b forearm
10c trunk
T1, T2 twisted part of a ringed strap

What is claimed is:

1. A shoulder brace for non-surgical treatment which includes a ringed strap configured to be fitted to a patient such that the ringed strap is linked between a distal clavicle end corresponding to a dislocated part in acromioclavicular joint dislocation or distal clavicle fracture and a part of the forearm adjacent to the elbow, wherein:

the ringed strap configured to lead the upper arm of the patient hanging down along the side of the trunk, the elbow flexed at an angle of 80-100°, and the forearm immobilized at a position corresponding to an internal rotation position of the shoulder at an angle of 20-40° on a horizontal plane of the shoulder and in an oblique and frontward direction from the trunk; and the ringed strap is fitted to the patient in a shape where the ringed strap (a) runs substantially vertically from the distal clavicle end toward a part of the ulnar side of the forearm adjacent to the elbow, (b) runs from the ulnar side of the forearm across the lower surface side of the forearm and turns to the radial side of the forearm, (c) runs from the radial side of the forearm across the front of the upper arm, and (d) runs up from the armpit on the affected-part side toward the back of the shoulder, and (e) runs across the back of the shoulder joint and reaches to the distal clavicle end.

2. The shoulder brace for non-surgical treatment according to claim 1, wherein the ringed strap is provided with a shoulder pad when in its position placed on the distal clavicle end.

3. The shoulder brace for non-surgical treatment according to claim 1, wherein the ringed strap is provided with a forearm trough for supporting the forearm of the patient.

4. The shoulder brace for non-surgical treatment according to claim 1, wherein the ringed strap is provided with a length adjusting portion.

5. The shoulder brace for non-surgical treatment according to claim 1 and wherein the ringed strap is twisted.

* * * * *